(12) United States Patent
Takayanagi et al.

(10) Patent No.: US 8,524,223 B2
(45) Date of Patent: Sep. 3, 2013

(54) BACILLUS SUBTILIS KS1 AS A PLANT DISEASE CONTROL AGENT

(75) Inventors: Tsutomu Takayanagi, Kofu (JP); Shunji Suzuki, Kofu (JP); Seiichi Furuya, Kofu (JP)

(73) Assignee: University of Yamanashi, Yamanashi (JP)

( * ) Notice: Subject to any disclaimer, the term of this patent is extended or adjusted under 35 U.S.C. 154(b) by 96 days.

(21) Appl. No.: 13/003,624

(22) PCT Filed: Jul. 3, 2009

(86) PCT No.: PCT/JP2009/003090
§ 371 (c)(1),
(2), (4) Date: Jan. 11, 2011

(87) PCT Pub. No.: WO2010/004713
PCT Pub. Date: Jan. 14, 2010

(65) Prior Publication Data
US 2011/0182871 A1    Jul. 28, 2011

(30) Foreign Application Priority Data
Jul. 11, 2008 (JP) .................................. 2008-181449

(51) Int. Cl.
*A01N 63/00* (2006.01)

(52) U.S. Cl.
USPC .................... 424/93.462; 424/246.1; 514/2.4; 435/222; 435/252.31

(58) Field of Classification Search
USPC ............ 424/93.462, 246.1; 435/222, 252.31; 514/2.4
See application file for complete search history.

(56) References Cited

U.S. PATENT DOCUMENTS

| | | | |
|---|---|---|---|
| 5,047,239 A | 9/1991 | Pusey | |
| 5,589,381 A | 12/1996 | Neyra et al. | |

FOREIGN PATENT DOCUMENTS

| | | | |
|---|---|---|---|
| JP | 05-051305 A | 3/1993 | |
| JP | 06-133763 A | 5/1994 | |
| JP | 08-175919 A | 7/1996 | |
| JP | 2001-206811 A | 7/2001 | |
| JP | 2003-277210 A | 10/2003 | |
| WO | 9315611 A1 | 8/1993 | |
| WO | 9821964 A1 | 5/1998 | |
| WO | 9850422 A1 | 11/1998 | |
| WO | 0058442 A1 | 10/2000 | |
| WO | 2008009795 A2 | 1/2008 | |

OTHER PUBLICATIONS

Hartman, John et al. Plant Pathology Fact Sheet: Fruit Rots of Grape. UK Cooperative Extension Service: PPF-FR-S-14. Oct. 2008. pp. 1-7.*
Becker, Ron et al. Agriculture & Natural Resources Fact Sheet: Managing Downy Mildew in Organic & Conventional Vine Crops. The Ohio Sate University Extension: HYG-3127-09. 2009. pp. 1-4.*
Furuya, Seiichi et al. Isolation and Characterization of *Bacillus subtilis* KS1 for the Biocontrol of Grapevine Fungal Diseases. Biocontrol Science and Technology. Mar. 2011. vol. 21(6). p. 705.*
Ryoo, Sung et al. Purification and Characterization of Antifungal Compounds Produced by *Bacillus subtilis* KS1. The Korean Journal of Mycology. Dec. 1996. vol. 24(4). p. 293.*
Ryoo, Sung. Purification and Characterization of Antifungal Compounds Produced by *Bacillus subtilis* KS1—English Translation. The Korean Journal of Mycology. Dec. 1996. vol. 24 No. 4. pp. 293-304.*
Ryoo, Sung. Purification and Characterization of Antifungal Compounds Produced by *Bacillus subtilis* KS1—Korean Publication. The Korean Journal of Mycology. Dec. 1996. vol. 24 No. 4. pp. 293-304.*
Alenius, et al., "*Bacillus subtilis* subs subtilis partial 16S rRNA gene, isolate OS-109", Database DDBJ/EBL/GenBank (online), Accessin No. AM237381, Jul. 17, 2009, 2 pages.
Furuya, et al., Prevention of grapevine diseases using antagonistic microbes, J. Asev Jpn., Jul. 12, 2008, pp. 72-73, vol. 19, No. 2. (English Abstract).

* cited by examiner

*Primary Examiner* — Susan Hanley
*Assistant Examiner* — Nghi Nguyen
(74) *Attorney, Agent, or Firm* — Browdy and Neimark, P.L.L.C.

(57) ABSTRACT

A microorganism inhibits the growth of various plant pathogens, and is not reduced in its efficacy even when the microorganism is used in combination with a chemical pesticide. The microorganism is *Bacillus subtilis* KS1 strain (NITE BP-569). The plant disease control agent comprises a culture of the microorganism as an active ingredient.

8 Claims, 2 Drawing Sheets

Bacteria causing grape ripe rot

KS1

BACILLUS SUBTILIS KS1 AS A PLANT DISEASE CONTROL AGENT

TECHNICAL FIELD

The present invention relates to a new species of *Bacillus subtilis* and a plant disease control agent using the bacterial cell and the culture of this microorganism.

BACKGROUND ART

Recently, there has been an increased interest in biological control techniques using a biological pesticide, which has less environmental load and a higher level of safety for humans and animals compared to chemical pesticides. However, a biological pesticide has a less instantaneous effect and a less therapeutic effect compared to chemical pesticides and can control only a limited range of pathogenic bacteria, and also loses the efficacy of the biological pesticide itself when used in combination with a chemical pesticide. Therefore, the market share of biological pesticides has currently remained only 0.4% of the total market of pesticides.

The technique using a biological pesticide utilizes an organism that is a natural enemy of phytopathogenic microorganisms and pests that cause plant diseases. *Bacillus subtilis* has been conventionally used as a biological pesticide against the bacteria causing botrytis rot in eggplants, tomatoes, or grapes, since it has antagonistic actions such as growth inhibition and a bactericidal action on phytopathogenic bacteria.

For example, a method for controlling plant diseases which includes a spore fraction prepared from a culture of *Bacillus* bacteria such as *Bacillus subtilis* so as to contain 50% or more by weight of spore based on the dry weight is conventionally known as a biological pesticide using *Bacillus subtilis* (see Patent Literature 1). Furthermore, in order to control plant diseases caused by *Phytophthora*, a disease control agent is known which includes the bacterial cell or the culture of *Bacillus* bacteria such as *Bacillus licheniformis*, and moreover organic acids and salts thereof produced by the bacteria as an active ingredient (see Patent Literature 2).

Furthermore, a plant disease control agent including the bacterial cell or the culture of *Bacillus sphaericus* is known (see Patent Literature 3), and a plant disease control agent using specific strains of *Bacillus subtilis* as an active ingredient is also known (see Patent Literatures 4 and 5).

However, the effects of the above-mentioned conventional plant disease control agents in the case of application to a grape are mediated by antagonistic actions by *Bacillus* bacteria that occupy the nutrition or living area on grape tissues. Therefore, although some preventive effect is produced by spraying prior to the occurrence of diseases, the agents have no therapeutic effect such as a bactericidal action, and thus have been unable to be used after the occurrence of diseases.

Furthermore, the above-mentioned conventional plant disease control agents are effective only for the bacteria causing grape botrytis rot among the pathogenic bacteria of the most common three grape diseases, grape botrytis rot, downy mildew, and ripe rot. Thus, they cannot be expected to have a control effect on the bacteria causing downy mildew and ripe rot other than grape botrytis rot or other pathogenic bacteria for grapes.

Furthermore, although the above-mentioned conventional plant disease control agents settle onto grape leaves, the level of settlement onto pericarps was low. It was also difficult to use a chemical pesticide for safety reasons since grape pericarps are also put into the mouth, and the control of diseases such as botrytis rot and ripe rot, which also occur in fruits, has been difficult.

CITATION LIST

Patent Literature

Patent Literature 1: Japanese Patent Application Laid-Open No. Hei. 8-175919
Patent Literature 2: Japanese Patent Application Laid-Open No. 2001-206811
Patent Literature 3: Japanese Patent Application Laid-Open No. 2003-277210
Patent Literature 4: Japanese Patent Application Laid-Open No. Hei. 6-133763
Patent Literature 5: Japanese Patent Application Laid-Open No. Hei. 5-51305

SUMMARY OF THE INVENTION

Problems to be Solved by the Invention

Therefore, the problem to be solved by the invention is to provide a novel microorganism which is expected to have both a preventive effect and a therapeutic effect and may be applied to various phytopathogenic bacteria, and whose effects are not reduced even when used in combination with a chemical pesticide, and a plant disease control agent using the microorganism.

Means for Solving the Problems

To solve the above-mentioned problem, the novel microorganism according to the present invention is characterized by being the *Bacillus subtilis* strain KS1 (NITE BP-569).

Furthermore, the plant disease control agent according to the present invention is characterized by including the culture and/or the microorganism bacterial cell of the above-mentioned *Bacillus subtilis* strain KS1 as an active ingredient.

Moreover, the plant disease control agent of the present invention acts effectively on the pathogenic bacteria that appear on the leaves or in the fruits of grapes. By way of example, the inventive plant disease control agent is effective against the bacteria causing botrytis rot, the bacteria causing downy mildew, the bacteria causing ripe rot, and the like.

Furthermore, since the plant disease control agent according to the present invention has resistance to chemical pesticides, it can be used in combination with a chemical pesticide.

Effects of the Invention

The *Bacillus subtilis* strain KS1 according to the present invention and the plant disease control agent that includes the culture or the microorganism bacterial cell of the *Bacillus subtilis* strain KS1 as an active ingredient can be expected to have a preventive effect and a therapeutic effect on a wide range of phytopathogenic bacteria such as the bacteria causing downy mildew, the bacteria causing botrytis rot, and the bacteria causing ripe rot.

MODE FOR CARRYING OUT THE INVENTION

Figure 1:
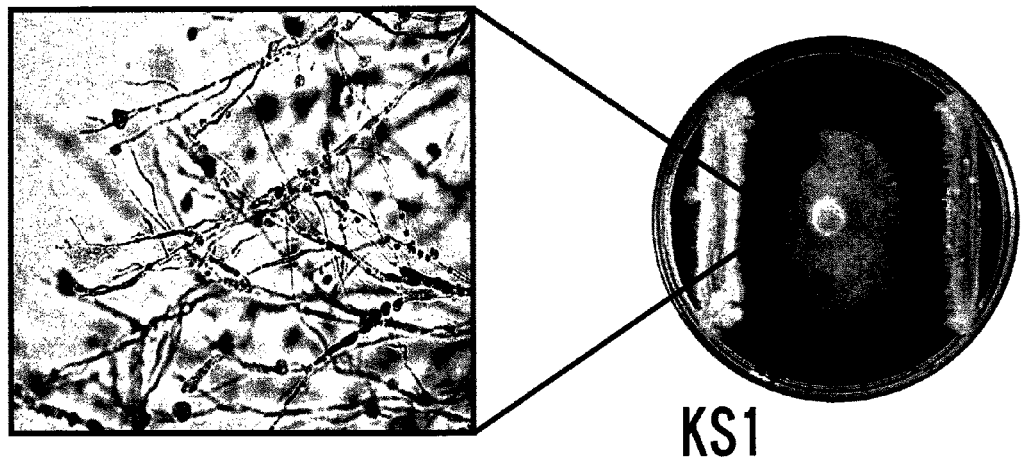
FIG. 1 a photomicrograph showing the tips of hyphae of the bacteria causing grape botrytis rot when the bacteria were grown in dual culture with the *Bacillus subtilis* strain KS1 of the present invention.

Hereinbelow, the present invention will be described in detail. The *Bacillus subtilis* strain KS1 according to the present invention is a bacterium discovered in grape pericarps and has features such as a high level of settlement on grape leaves. Hereinbelow, bacteriological properties of the *Bacillus subtilis* strain KS1 are listed.

A. Morphology of Bacteria
(1) Shape: bacillus
(2) Size: 0.8×3 to 5 μm
(3) Motility: no
B. Morphology of Colony (Incubation at 31° C. for 2 Days)
(1) Name of the Medium: SCD agar medium
(2) Shape: irregular circle
(3) Size: 5 mm
(4) Elevation: flat
(5) Margin Shape: undulate
(6) Surface Shape: wrinkled
(7) Texture: mucoid
(8) Transparency: opaque
(9) Luster: dull luster
(10) Color: light beige
C. Physiological Properties

TABLE 1

| 1  | Gram staining               | (+) |
|----|-----------------------------|-----|
| 2  | Sporulation                 | (+) |
| 3  | Catalase                    | (+) |
| 4  | β-galactosidase             | (+) |
| 5  | Arginine dihydrolase        | (−) |
| 6  | Lysine decarboxylase        | (−) |
| 7  | Ornithine decarboxylase     | (−) |
| 8  | Citrate utilization         | (−) |
| 9  | H₂S production              | (−) |
| 10 | Urease                      | (−) |
| 11 | Tryptophan deaminase        | (−) |
| 12 | Indole production           | (−) |
| 13 | Acetoin production          | (+) |
| 14 | Gelatin liquefaction        | (+) |
| 15 | Nitrate reduction           | (+) |
|    | Fermentation/oxidation      |     |
| 16 | Glycerol                    | (+) |
| 17 | Erythritol                  | (−) |
| 18 | D-arabinose                 | (−) |
| 19 | L-arabinose                 | (+) |
| 20 | Ribose                      | (+) |
| 21 | D-xylose                    | (+) |
| 22 | L-xylose                    | (−) |
| 23 | Adonitol                    | (−) |
| 24 | Methyl-β-D-xylopyranoside   | (−) |
| 25 | Galactose                   | (−) |
| 26 | Glucose                     | (+) |
| 27 | Fructose                    | (+) |
| 28 | Mannose                     | (+) |
| 29 | Sorbose                     | (+) |
| 30 | Rhamnose                    | (−) |
| 31 | Dulcitol                    | (−) |
| 32 | Inositol                    | (+) |
| 33 | Mannitol                    | (+) |
| 34 | Sorbitol                    | (+) |
| 35 | Methyl-α-D-mannopyranoside  | (−) |
| 36 | Methyl-α-D-glucopyranoside  | (+) |
| 37 | N-acetylglucosamine         | (+) |
| 38 | Amygdalin                   | (−) |
| 39 | Arbutin                     | (−) |
| 40 | Esculin                     | (+) |
| 41 | Salicin                     | (−) |

TABLE 1-continued

| 42 | Cellobiose     | (−) |
|----|----------------|-----|
| 43 | Maltose        | (+) |
| 44 | Lactose        | (−) |
| 45 | Melibiose      | (−) |
| 46 | Sucrose        | (+) |
| 47 | Trehalose      | (+) |
| 48 | Inulin         | (−) |
| 49 | Melezitose     | (−) |
| 50 | Raffinose      | (−) |
| 51 | Starch         | (−) |
| 52 | Glycogen       | (−) |
| 53 | Xylitol        | (−) |
| 54 | Gentiobiose    | (−) |
| 55 | D-turanose     | (+) |
| 56 | D-lyxose       | (−) |
| 57 | D-tagatose     | (−) |
| 58 | D-fucose       | (−) |
| 59 | L-fucose       | (−) |
| 60 | D-arabitol     | (−) |
| 61 | L-arabitol     | (−) |
| 62 | Gluconate      | (−) |
| 63 | 2-ketogluconate| (−) |
| 64 | 5-ketogluconate| (−) |

(+): Positive
(−): Negative
(±): False-positive

The base sequence of rDNA corresponding to the 16S subunit is as follows.

[SEQ ID NO: 1]
GACGAACGCTGGCGGCGTGCCTAATACATGCAAGTCGAGCGGACAGAT

GGGAGCTTGCTCCCTGATGTTAGCGGCGGACGGGTGAGTAACACGTGG

GTAACCTGCCTGTAAGACTGGGATAACTCCGGGAAACCGGGGCTAATA

CCGGATGGTTGTTTGAACCGCATGGTTCGAACATAAAAGGTGGCTTCG

GCTACCACTTACAGATGGACCCGCGGCGCATTAGCTAGTTGGTGAGGT

AATGGCTCACCAAGGCGACGATGCGTAGCCGAACCTGAGAGGGTGATC

GGCCACACTGGGACTGAGACACGGCCCAGACTCCTACGGGAGGCAGCA

GTAGGGAATCTTCCGCAATGGACGAAAGTCTGACGGAGCAACGCCGCG

TGAGTGATGAAGGTTTTCGGATTGTAAAGCTCTGTTGTTAGGGAAGAA

CAAGTACCGTTCGAATAGGGGCGACCTTGACGGTACCTAACCAGAAA

GCCACGGCTAACTACGTGC

This bacterial strain was identified as *Bacillus subtilis* on the basis of the above-mentioned bacteriological properties and SEQ ID NO: 1, the base sequence of 16SrDNA, and designated *Bacillus subtilis* strain KS1. Incidentally, this *Bacillus subtilis* strain KS1 was deposited with the National Institute of Technology and Evaluation, Patent Microorganisms Depositary (2-5-8 Kazusakamatari, Kisarazu-shi, Chiba) on May 13, 2008 and deposited under Accession No. "NITE P-569." The strain was converted to an international deposit under the Budapest Treaty on May 20, 2009 and received Accession No. "NITE BP-569."

Incidentally, the *Bacillus subtilis* strain KS1 according to the present invention is not limited to the base sequence that is completely identical to the base sequence of 16SrDNA shown in SEQ ID NO: 1 described above. The inventive *Bacillus subtilis* strain KS1 also includes those that even when the strains are composed of a base sequence in which one or several bases of the base sequence are deleted, substituted, or other bases are added thereto, have similar traits to the *Bacillus subtilis* strain KS1 regarding a plant disease control action, especially a grape disease control action.

The culture medium that can be used in the present invention is not particularly limited as long as the strain of the present invention can grow in culture. For example, glucose, sucrose, casein, yeast extract, meat extract, and the like are used as a carbon source, and yeast extract, meat extract, polypeptone, peptone, trypsin, and the like are used as a nitrogen source. Sodium, potassium, magnesium, iron, calcium, and the like are also added as other nutrients.

Culture in the present invention may be performed under aerobic conditions, for example with aeration-agitation, by shaking culture, by a solid culture method, or the like. Although the culture condition is not particularly limited, temperatures ranging from 30 to 37° C., pH ranging from 6.5 to 7.5, and time periods ranging from 12 to 48 hours are suitable.

The *Bacillus subtilis* strain KS1 cultured as described above may be used without being separated from the culture, or used after the separation of bacterial cells by centrifugation. Furthermore, in the case of using this strain as a plant disease control agent, it may be formulated with various additives such as a surfactant (for example, sorbitan monolaurate commonly known as Tween20) and a spreader (for example, SABUMAHJI from Syngenta Japan) and used as a granule, an emulsifiable concentrate, a water dispersible powder, a flowable, and the like.

The bacterial cell or the culture thus prepared of the *Bacillus subtilis* strain KS1 may be applied to a plant body or soil, thereby controlling plant diseases. The control agent of the present invention has a significant effect on the control of grape diseases caused by, for example, the bacteria causing grape botrytis rot, the bacteria causing grape ripe rot, the bacteria causing grape white root-rot, the bacteria causing grape downy mildew, and the like. In addition, the control agent also has an effect on the control of the bacteria causing botrytis rot and the bacteria causing anthracnose, which infect plants other than a grape, such as strawberries and cucumbers.

The application method of the control agent is selected as appropriate depending on the form of the formulation, the type of the plant, and the type and degree of the disease. For example, a method in which a liquefied control agent is used for ground application of the liquid formulation or aerial application of the liquid formulation, a method of directly spraying or applying the control agent onto plant leaves, moreover, a method by immersion into a solution of the control agent, or the like may be selected.

Although the application amount varies depending on, for example, the type of diseases and plants for application, for example, the control agent is applied at a concentration of $1.5 \times 10^8$ cells/mL (containing 0.02% Tween20) and using 5 liters per are of the field.

EXAMPLES

Hereinbelow, the present invention will be described in detail on the basis of Examples, but, of course, the present invention is not limited to these examples.

Example 1

Example of Culture

A portion of the *Bacillus subtilis* strain KS1 according to the present invention taken by means of a platinum loop was inoculated on a broth medium (10 g of meat extract, 10 g of peptone, 5 g of sodium chloride, and 1 L of water), and incubated with shaking at 150 rpm for 12 hours at 37° C. to obtain the culture medium. The bacterial cells of strain KS1 were harvested from this culture medium by centrifugation. Then, the harvested bacterial cells of strain KS1 were adjusted with water to 1.3 to $1.5 \times 10^8$ cells/mL and Tween20 (at a final concentration of 0.02%) was added as a surfactant, thereby formulating a flowable.

Example 2

Application to Pathogenic Bacteria, Test 1

In this example, a test to determine the control effect of *Bacillus subtilis* strain KS1 on the bacteria causing grape downy mildew was performed. The flowable prepared in Example 1 described above was sprayed onto ten-year-old Koshu grapes (espalier) planted in the experimental field of the Institute of Enology and Viticulture, Yamanashi University, and the effect was examined. Because completely pesticide-free farming has been performed since 2005 (Heisei 17) in this experimental field, grape downy mildew frequently occurs every year. Thus, the above-mentioned flowable was sprayed evenly on young shoots of grapes once per week, every week from May 11 to August 17 in 2007 (Heisei 19). The application rate was approximately five liters per are of the field. In parallel, as a comparative example to this example, a commercially available microbial pesticide, a Botokiller water dispersible powder, (registered trademark, Idemitsu Kosan Co., Ltd.) was sprayed at the same concentration and at the same frequency. An untreated area where no agents were sprayed was also compared.

Incidence of downy mildew was examined on Aug. 21, 2007 (Heisei 19). Disease incidence (%) was calculated on the basis of the number of leaves that had developed symptoms of downy mildew, and also, disease severity ($cm^2$) was calculated on the basis of the total area with symptoms in the experimental field. These results are shown in Table 2.

TABLE 2

| | Disease incidence(%) | Disease severity($cm^2$) |
|---|---|---|
| *B. subtilis* KS1 | 10 | 4 |
| Botokiller water dispersible powder | 50 | 301 |
| Untreated area | 60 | 299 |

As is clear from the results in Table 2 described above, *Bacillus subtilis* strain KS1 was found to have a control effect, particularly a very high level of preventive effect on the bacteria causing grape downy mildew.

Example 3

Application to Pathogenic Bacteria, Test 2

In this example, a test to determine a control effect of *Bacillus subtilis* strain KS1 on the bacteria causing botrytis rot and the bacteria causing ripe rot was performed. First, the pathogenic bacteria to be examined (the bacteria causing botrytis rot and the bacteria causing ripe rot) were precultured on a PDA medium (one containing potato extract and glucose in agar) at 25° C. for about 5 days. Next, a disk with a diameter of 6 mm was hollowed out of the grown-up mycelium using a cork borer and placed in the center of a new petri dish containing the PDA medium. Furthermore, dual culture was performed by linearly smearing *Bacillus subtilis* strain KS1 on the end of the same petri dish, and interaction between the bacterial lawn of the examined bacteria and *Bacillus subtilis* strain KS1 was monitored.

Figure 2:
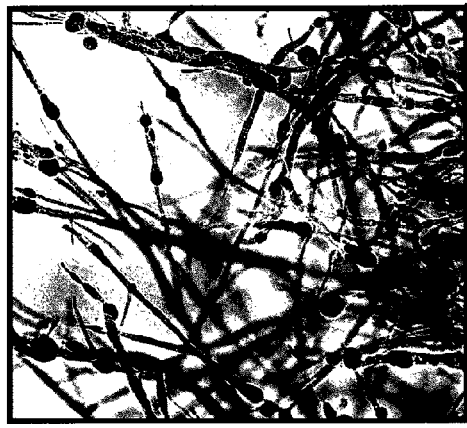
FIG. 2 a photomicrograph showing the tips of hyphae of the bacteria causing grape ripe rot when the bacteria were grown in dual culture with the *Bacillus subtilis* strain KS1 of the present invention.
Figure 2:
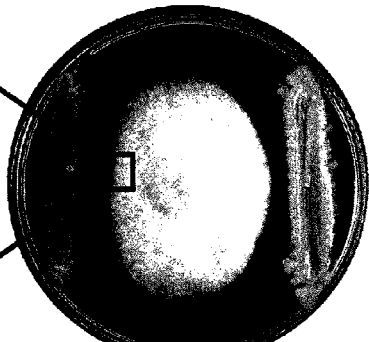

FIGS. 1 and 2 are photomicrographs (200×) showing the tips of hyphae of the examined bacteria after 3 days of dual culture at 25° C. These photographs show the state in which the tips of hyphae of both the bacteria causing botrytis rot and the bacteria causing ripe rot swelled and ruptured and the growth of the pathogenic bacteria was inhibited. One of the mechanisms of this growth inhibition is presumed to result from antibacterial substances produced by *Bacillus subtilis* strain KS1. As is clear from this example, it was confirmed that *Bacillus subtilis* strain KS1 had a control effect, particularly a therapeutic effect due to a bactericidal action, on the bacteria causing botrytis rot or the bacteria causing ripe rot, which are among the main pathogenic bacteria for grapes.

Example 4

Drug Resistance Test

In this example, a test for resistance of *Bacillus subtilis* strain KS1 to chemical pesticides was performed. First, the YBS medium (one containing yeast extract and meat extract in agar) containing the chemical pesticide of interest was prepared in a petri dish. The concentration (ppm) of the chemical pesticide at this time was the same as a general application concentration. Next, *Bacillus subtilis* strain KS1 was smeared on the surface of the above-mentioned medium containing the chemical pesticide and incubated at 37° C. for 2 days. As a control area, a test for resistance of *Bacillus subtilis* isolated from a Botokiller water dispersible powder to chemical pesticides was performed in parallel. In this case, the suspension of the Botokiller water dispersible powder was spread on the YBS medium and the bacteria that appeared after overnight incubation at 37° C. were considered as the bacteria constituting a Botokiller water dispersible powder. In the resistance test, the bacteria constituting a Botokiller water dispersible powder were smeared on the surface of the medium containing a chemical pesticide and incubated at 37° C. for 2 days, as is the case with the above-mentioned *Bacillus subtilis* strain KS1.

After 2 days of incubation at 37° C., the *Bacillus subtilis* strain KS1 and the bacteria constituting a Botokiller water dispersible powder were macroscopically observed to see whether they had grown or not. When the growth of the bacteria was observed (when the bacteria had grown greatly), they were considered to be resistant to the chemical pesticide.

Table 3 indicates the results of resistance tests on 11 chemical pesticides that are currently commonly used in viticulture.

TABLE 3

| Chemical pesticides used in viticulture | Concentration (ppm) | *B. Subtilis* KS1 | *B. subtilis* used in a Botokiller water dispersible powder |
|---|---|---|---|
| Azoxystrobin | 150 | + | + |
| Benomyl | 200 | + | + |
| Carbaryl | 850 | + | + |
| Diethofencarb | 50 | + | + |
| Fenhexamid | 100 | + | + |
| Fenitrothin | 400 | + | + |
| Imidacloprid | 100 | + | + |
| Maneb | 100 | + | − |
| Permerhrin | 100 | + | + |
| Procymidone | 20 | + | + |
| Thiophanate-methyl | 100 | + | + |

+ Good growth
− No growth

According to the test results, the *Bacillus subtilis* strain KS1 of the present invention showed resistance to all the tested chemical pesticides and also showed resistance to Maneb (product name: Maneb-Dithane M water dispersible powder) that is widely used especially for downy mildew, ripe rot, and the like. Therefore, the possibility of effective combined application of the strain KS1 with chemical pesticides is suggested. Incidentally, the bacteria constituting a Botokiller water dispersible powder showed no resistance to the above-mentioned Maneb.

INDUSTRIAL APPLICABILITY

The *Bacillus subtilis* strain KS1 of the present invention is effective against a wide variety of grape diseases such as the bacteria causing downy mildew, the bacteria causing botrytis rot, and the bacteria causing ripe rot. This wide control effect means that the KS1 strain can decrease the number or the application amount of agents that are currently applied to control grape diseases (chemical pesticides and biological pesticides). Since the KS1 strain produces an effect such as a contribution to the reduction of labor or cost in viticulture in addition to environmental conservation, it has an industrial applicability as a biological pesticide.

The invention claimed is:

1. An isolated microorganism being the *Bacillus subtilis* strain KS1 (NITE BP-569).

2. A plant disease control agent, comprising a culture of the microorganism of claim 1 as an active ingredient.

3. The plant disease control agent according to claim 2, wherein the microorganism inhibits the growth of a phytopathogenic fungus that appears on leaves or in fruits of grapes.

4. The plant disease control agent according to claim 2, wherein the microorganism has resistance to a chemical pesticide.

5. The plant disease control agent according to claim 2, wherein the microorganism inhibits the growth of a fungus causing botrytis rot, a fungus causing downy mildew, and a fungus causing ripe rot.

6. The agent of claim 4 which is resistant to 150 ppm Azoxystrobin, 200 ppm Benomyl, 850 ppm Carbaryl, 50 ppm Diethofencarb, 100 ppm Fenhexamid, 400 ppm Fenitrothin, 100 ppm Imidacloprid, 100 ppm Maneb, 100 ppm Permethrin, 20 ppm Procymidone, and 100 ppm Thiophanate-methyl.

7. A method of inhibiting the growth of a phyopathogenic fungus that appears on leaves or in fruits of grapes that comprising applying to the leaves or fruits of grapes a fungal growth-inhibitory amount of the agent of claim 2.

8. The method of claim 7, wherein boturitis rot, downy mildew, and ripe rot are inhibited.

* * * * *

SEQUENCE LISTING

<160> NUMBER OF SEQ ID NOS: 1

<210> SEQ ID NO 1
<211> LENGTH: 499
<212> TYPE: DNA
<213> ORGANISM: Bacillus subtilis KS1

<400> SEQUENCE: 1

```
gacgaacgct ggcggcgtgc ctaatacatg caagtcgagc ggacagatgg gagcttgctc       60
cctgatgtta gcggcggacg ggtgagtaac acgtgggtaa cctgcctgta agactgggat      120
aactccggga aaccggggct aataccggat ggttgtttga accgcatggt tcgaacataa      180
aaggtggctt cggctaccac ttacagatgg acccgcggcg cattagctag ttggtgaggt      240
aatggctcac caaggcgacg atgcgtagcc gaacctgaga gggtgatcgg ccacactggg      300
actgagacac ggcccagact cctacgggag gcagcagtag ggaatcttcc gcaatggacg      360
```

```
                                                    -continued aaagtctgac ggagcaacgc cgcgtgagtg atgaaggttt tcggattgta aagctctgtt    420
gttagggaag aacaagtacc gttcgaatag ggggcgacct tgacggtacc taaccagaaa    480
gccacggcta actacgtgc                                                 499
```